United States Patent [19]

Kühle et al.

[11] Patent Number: 4,515,812
[45] Date of Patent: May 7, 1985

[54] COMBATING FUNGI WITH N-SULPHENYLATED UREAS

[75] Inventors: Engelbert Kühle, Berg.-Gladbach; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 481,700

[22] Filed: Apr. 4, 1983

Related U.S. Application Data

[62] Division of Ser. No. 290,899, Aug. 7, 1981, Pat. No. 4,397,869.

[30] Foreign Application Priority Data

Aug. 27, 1980 [DE] Fed. Rep. of Germany ....... 3032327

[51] Int. Cl.³ ..................... C07C 127/19; A01N 47/28
[52] U.S. Cl. ............................. 514/592; 260/453 RW; 260/465 D; 514/522; 564/39
[58] Field of Search ................... 564/39; 260/453 RW, 260/465 D; 424/304, 322

[56] References Cited

U.S. PATENT DOCUMENTS

| | | | |
|---|---|---|---|
| 3,344,153 | 9/1967 | Kühle et al. | 260/453 RW X |
| 3,496,208 | 2/1970 | Bachman et al. | 260/453 RW |
| 3,502,705 | 3/1970 | Brown | 564/39 X |
| 3,980,693 | 9/1976 | Kühle et al. | 260/453 RW X |
| 4,012,436 | 3/1977 | Moore | 564/39 X |
| 4,137,068 | 1/1979 | Perronnet et al. | 260/453 RW X |
| 4,382,956 | 5/1983 | Kühle et al. | 424/322 |

Primary Examiner—Thomas A. Waltz
Attorney, Agent, or Firm—Sprung, Horn, Kramer & Woods

[57] ABSTRACT

N-Sulphenylated ureas of the formula

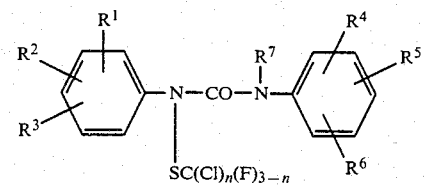

in which
  $R^1$ to $R^6$ each independently is hydrogen, halogen, nitro, cyano, alkyl, alkoxy, alkylmercapto, trihalogenomethyl-, trihalogenomethoxy or trihalogenomethylmercapto,
  $R^7$ is hydrogen or alkyl, and
  n is 0, 1, 2 or 3, which possess fungicidal properties.

13 Claims, No Drawings

COMBATING FUNGI WITH N-SULPHENYLATED UREAS

This is a division of application Ser. No. 290,899, filed Aug. 7, 1981, now U.S. Pat. No. 4,397,869.

The present invention relates to certain new N-sulphenylated ureas, to a process for their preparation and to their use as fungicides.

It has already been disclosed that N-trihalogenomethane-sulphenyl-dicarboximides have a fungicidal activity. Thus, for example, N-trichloromethanesulphenyl-tetrahydrophthalimide has been used for many years as a leaf fungicide in various crops (see U.S. Pat. No. 2,553,770). The activity of this product is not always satisfactory. Furthermore, N-sulphenylated carbamoyl compounds with a trihalogenomethanesulphenyl group are also fungicidally active; the fungicidal action of this class of compound is also not always sufficient (in this context, see DT-OS (German Published Specification) No. 2,354,492).

The present invention now provides, as new compounds, the N-sulphenylated ureas of the general formula

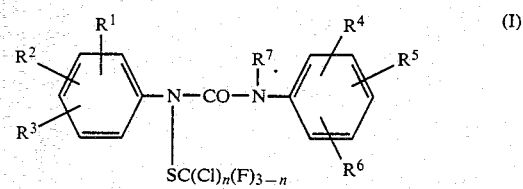

in which
R$^1$–R$^6$ are selected independently and each represents hydrogen, halogen, nitro, cyano, alkyl, alkoxy, alkylmercapto, trihalogenomethyl, trihalogenomethoxy or trihalogenomethylmercapto,
R$^7$ represents hydrogen or alkyl and
n denotes 0, 1, 2 or 3.

Compounds of the formula (I), in which
R$^1$–R$^6$ are selected independently and each represents hydrogen, halogen, nitro, cyano, C$_{1-4}$-alkyl, C$_{1-4}$-alkoxy, C$_{1-4}$-alkylmercapto, trihalogenomethyl, trihalogenomethoxy or trihalogenomethylmercapto,
are preferred.

Compounds of the formula (I) in which R$^1$–R$^6$ each represents a hydrogen, chlorine, trifluoromethyl or methoxy, are particularly preferred.

The compounds according to the invention have an excellent fungicidal action. It is surprising that the compounds according to the invention have a more powerful fungicidal action than the very closely related compounds known from the state of the art.

The invention also provides a process for the preparation of an N-sulphenylated urea of the formula (I) above, in which an N-sulphenylated carbamic acid fluoride of the general formula

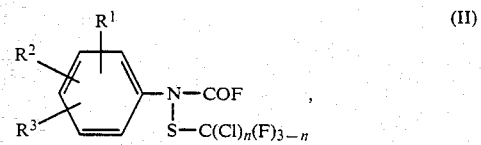

in which R$^1$–R$^3$ and n have the abovementioned meanings, is reacted with an aniline of the general formula

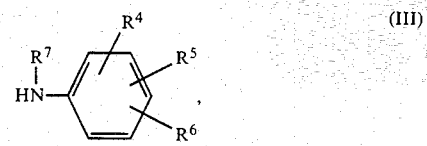

in which R$^4$–R$^7$ have the abovementioned meanings in the presence of a diluent and an acid-binding agent.

When N-(fluorodichloromethylsulphenyl)-4-chlorophenylcarbamic acid fluoride and 3,4-dichloroaniline are used as starting materials, the course of the reaction can be represented by the following equation:

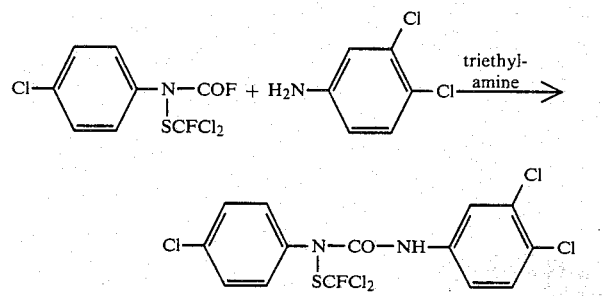

The formula (II) provides an unambiguous definition of the N-sulphenylated carbamic acid fluorides to be used as starting materials. In this formula, n preferably represents the number 2 or 3. The radicals R$^1$–R$^3$ each preferably denotes hydrogen, chlorine, nitro, cyano, lower alkyl, lower alkoxy, lower alkylmercapto, trifluoromethyl, difluorochloromethyl, trifluoromethoxy or trifluoromethylmercapto. These compounds are known (DE-AS (German Published Specification) No. 1,297,095), and they can be prepared in a known manner from arylcarbamic acid fluorides and trihalogenomethanesulphenyl chloride in the presence of an acid-binding agent.

Examples which may be mentioned are: N-(trichloromethylsulphenyl)- and N-(fluorodichloromethylsulphenyl)phenylcarbamic acid fluoride, and the corresponding N-(trichloromethylsulphenyl)- and N-(fluorodichloromethylsulphenyl)-arylcarbamic acid fluorides of 2-chloroaniline, 3,4-dichloroaniline, 3-nitroaniline, 4-toluidine, 4-isopropylaniline, 3-chloro-4-methoxyaniline, 2-chloro-4-methylmercaptoaniline, 2-chloro-4-trifluoromethylaniline, 4-difluorochloromethylaniline, 3-chloro-4-trifluoromethoxyaniline and 3-trifluoromethylmercaptoaniline.

The formula (III) provides a definition of the anilines also required for the reaction. In this formula, the radicals R$^4$–R$^6$ each preferably represents hydrogen, chlorine, nitro, cyano, lower alkyl, lower alkoxy, lower alkylmercapto, trifluoromethyl, trifluoromethoxy, difluorochloromethoxy, trifluoromethylmercapto or difluorochloromethylmercapto. R$^7$ preferably represents hydrogen or lower alkyl, in particular methyl.

The anilines of the formula (III) are known, and they can be prepared in a manner which is in itself known, by reduction of the corresponding nitro compounds.

The compounds according to the invention are preferably prepared in organic solvents. These include, as preferences, ethers, such as diethyl ether, tetrahydrofuran and dioxane; hydrocarbons, such as toluene; and chlorinated hydrocarbons, such as chloroform and chlorobenzene.

An acid-binding agent is added to the reaction mixture in order to bond the hydrogen fluoride formed during the reaction. Tertiary amine, such as pyridine or triethylamine, or an inorganic base, such as an alkali metal hydroxide or alkaline earth metal hydroxide or alkali metal carbonate, is preferably used. It is also possible for the aniline used for the reaction to be employed in, say, a twofold excess.

The reaction temperatures can be varied within a substantial range; the reaction is in general carried out at between 0° and 100° C., preferably at from 20° to 50° C.

The reaction is in general carried out under normal pressure. The starting compounds are employed in equimolar ratio. An excess of either of the reactants provides no substantial advantages. After the reaction has taken place, working up is carried out in the customary manner.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

They display a particularly good activity against parasitic fungi on above-ground parts of plants, such as, for example, against Phytophthora species and against the apple scab causative organism (Fusicladium dendriticum). They also exhibit an activity against *Pyricularis oryzae*.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol, or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphorates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

(a) Preparation of the starting compounds:

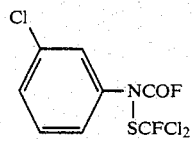
(a)

185 ml of triethylamine were added dropwise to a solution of 212 g of 3-chlorophenylcarbamic acid fluoride (obtained from 3-chlorophenyl isocyanate and anhydrous hydrofluoric acid) and 217 g of fluorodichloromethanesulphenyl chloride in 600 ml of chlorobenzene. The temperature was kept below 30° C. by cooling with ice-water. The mixture was stirred for a while, water was added and, after drying, the organic solution was concentrated in vacuo. 304 g of N-(fluorodichloromethylsulphenyl)-3-chlorophenylcarbamic acid fluoride of boiling point 85° to 90° C./0.05 mm Hg were obtained by distillation. According to gas chromatography, the product was 96.4% pure.

The following compounds were obtained analogously:

| Intermediate No. | Formula | Boiling point (°C./mm Hg) |
|---|---|---|
| b | 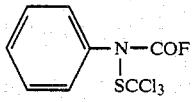 | 95–100°/0.05 |
| c | 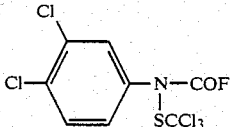 | 130–135°/0.05 |
| d | 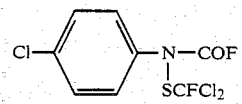 | 94–100°/0.05 |
| e | 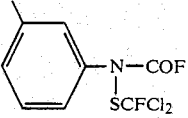 | 82°/0.05 |
| f | 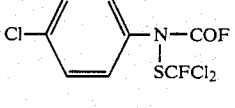 | 125°/0.12 |
| g | 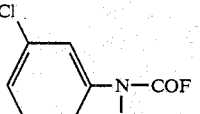 | 108–110°/0.15 |

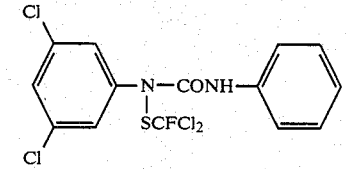
(b)

10.2 g (0.03 mole) of N-(fluorodichloromethanesulphenyl)-3,5-dichlorophenylcarbamic acid fluoride were dissolved in 100 ml of toluene. A solution of 6 g (0.07 mole) of aniline in 20 ml of toluene was added dropwise thereto. During this addition, the temperature rose slightly. The mixture was stirred at 50° to 60° C. for one hour and, after adding water, was acidified with hydrochloric acid, and the toluene solution was concentrated. 12 g of N-(fluorodichloromethylsulphenyl)-N-3,5-dichlorophenyl-N'-phenylurea of melting point 100° to 102° C. were obtained as the residue.

The following compounds according to the invention could be prepared in an analogous manner:

| Compound No. | Formula | Melting point (°C.) |
|---|---|---|
| 2. | 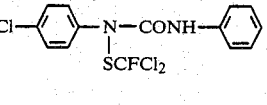 | 104–105° |
| 3. | 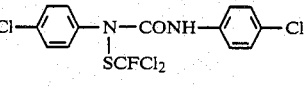 | 125–126° |
| 4. | 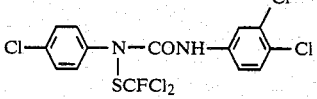 | 158–162° |
| 5. | 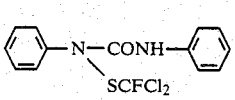 | 109–111° |

-continued

| Compound No. | Formula | Melting point (°C.) |
|---|---|---|
| 6. | C6H5-N(SCCl3)-CONH-C6H5 | 111-112° |
| 7. | 3-Cl-C6H4-N(SCFCl2)-CONH-C6H5 | 97-98° |
| 8. | 3-CF3-C6H4-N(SCFCl2)-CONH-C6H5 | 100-101° |
| 9. | 3,4-Cl2-C6H3-N(SCFCl2)-CONH-C6H5 | 123-125° |
| 10. | 3,4-Cl2-C6H3-N(SCCl3)-CONH-C6H5 | 129-131° |
| 11. | C6H5-N(SCFCl2)-CONH-C6H4-4-Cl | 80-85° |
| 12. | 3-Cl-C6H4-N(SCFCl2)-CONH-C6H4-4-Cl | 83-88° |
| 13. | C6H5-N(SCFCl2)-CONH-C6H4-4-OCH3 | 94-96° |
| 14. | C6H5-N(SCCl3)-CONH-C6H4-4-OCH3 | 104-106° |
| 15. | 3,4-Cl2-C6H3-N(SCFCl2)-CONH-C6H4-4-OCH3 | 128-131° |
| 16. | 3-CF3-C6H4-N(SCFCl2)-CONH-C6H4-4-OCH3 | 92° |
| 17. | 3,4-Cl2-C6H3-N(SCFCl2)-CONH-C6H4-3-OCH3 | 127-132° |
| 18. | 3,4-Cl2-C6H3-N(SCFCl2)-CONH-C6H4-4-OCH3 | 108° |

The fungicidal activity of the compounds of this invention is illustrated by the following examples wherein, the compounds according to the present invention are each identified by the number (given in brackets) from Example 1 hereinabove:

EXAMPLE 2

Phytophthora Test (tomato)/protective
Solvent: 4.7 parts by weight of acetone
Emulsifier: 0.3 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were inoculated with an aqueous spore suspension of Phytophthora infestans.

The plants were placed in an incubation cabin at 100% relative atmospheric humidity and at about 20° C. Evaluation was carried out 4 days after the inoculation.

In this test, a clearly superior activity compared with the prior art was shown, for example, by the compounds (1), (2), (3), (5), (7), (8), (9), (11), (12), (13), (14), (15) and (16).

EXAMPLE 3

Fusicladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (Fusicladium dendriticum) and incubated for 18 hours in a humidity chamber at 18° to 20° C. and at a relative atmospheric humidity of 100%.

The plants were then brought again into a greenhouse for 14 days.

15 days after inoculation, the infection of the seedlings was determined. The assessment data were converted to percent infection. 0% denoted no infection and 100% denoted that the plants were totally infected.

In this test, for example, the following compounds snowed a superior activity compared with the prior art: (1), (2), (4), (7), (8), (11), (12), (13) and (17).

EXAMPLE 4

Fusarium nivale test (rye)/seed treatment

The active compounds were used as dry dressings. These were prepared by extending the particular active compound with a ground mineral to give a finely pulverulent mixture, which ensured uniform distribution on the seed surface.

To apply the dressing, the infected seed was shaken with the dressing in a closed glass flask for 3 minutes.

2 batches of 100 grains of the rye were sown 1 cm deep in standard soil and were cultivated in a greenhouse at a temperature of about 10° C. and a relative atmospheric humidity of about 95%, in seedboxes which were exposed to light for 15 hours daily.

About 3 weeks after sowing, the plants were evaluated for symptoms of snow mold.

In this test, a clearly superior activity compared with the prior art was shown, for example, by the compounds (5), (11) and (12).

It will be appreciated that the instant specification and examples are set forth by way of illustration and not limitation, and that various modifications and changes may be made without departing from the spirit and scope of the present invention.

We claim:

1. An N-sulphenylated urea of the formula

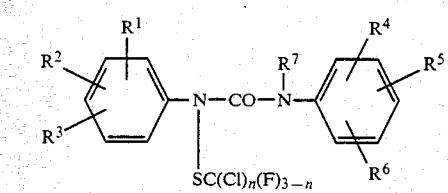

in which
R$^1$ to R$^6$ each independently is hydrogen, halogen, nitro, cyano, alkyl, alkoxy, alkylmercapto, trihalogenomethyl-, trihalogenomethoxy or trihalogenomethylmercapto,
R$^7$ is hydrogen or alkyl, and
n is 0, 1 or 2,
both of the phenyl rings being substituted by other than hydrogen.

2. A compound according to claim 1, in which
R$^1$ to R$^6$ each independently is hydrogen, halogen, nitro, cyano, C$_{1-4}$-alkyl, C$_{1-4}$-alkoxy, C$_{1-4}$-alkylmercapto, trihalogenomethyl, trihalogenomethoxy or trihalogenomethylmercapto.

3. A compound according to claim 1, in which
R$^1$ to R$^6$ each independently is hydrogen, chlorine, trifluoromethyl or methoxy,
R$^7$ is hydrogen or, C$_{1-4}$-alkyl, and
n is 2 or 3.

4. A compound according to claim 1, wherein such compound is N-(fluorodichloromethylsulphenyl)-N,N$^1$-bis-(4-chlorophenyl)-urea of the formula

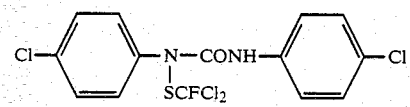

5. A compound according to claim 1, wherein such compound is N-(fluorodichloromethylsulphenyl)-N-(4-chlorophenyl)-N$^1$-(3,4-dichlorophenyl)-urea of the formula

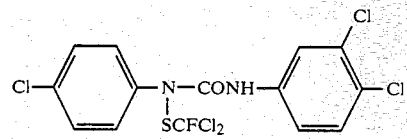

6. A compound according to claim 1, wherein such compound is N-(fluorodichloromethylsulphenyl)-N-(3-chlorophenyl)-N$^1$-(4-chlorophenyl)-urea of the formula

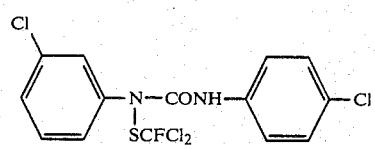

7. A compound according to claim 1, wherein such compound is N-(fluorodichloromethylsulphenyl)-N-(3,4-dichlorophenyl)-N$^1$-(4-methoxyphenyl)-urea of the formula

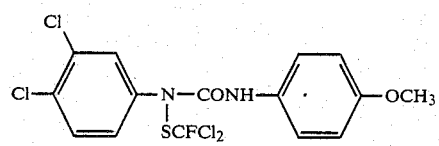

8. A compound according to claim 1, wherein such compound is N-(fluorodichloromethylsulphenyl)-N-(3-trifluoromethylphenyl)-N$^1$-(4-methoxyphenyl)-urea of the formula

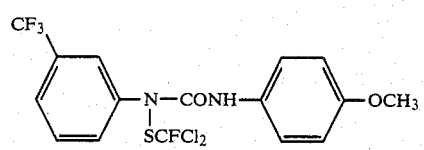

9. A compound according to claim 1, wherein such compound is N-(fluorodichloromethylsulphenyl)-N-(3,4-dichlorophenyl)-N$^1$-(3-methoxyphenyl)-urea of the formula

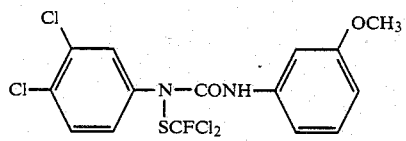

10. A compound according to claim 1, wherein such compound is N-(fluorodichloromethylsulphenyl-N-(4-chlorophenyl)-N$^1$-(4-methoxyphenyl)-urea of the formula

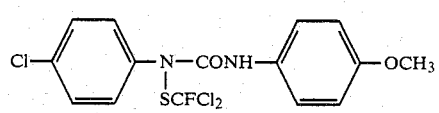

11. A fungicidal composition comprising a fungicidally effective amount of a compound according to claim 1 in admixture with a diluent.

12. A method of combating fungi comprising applying to the fungi, or to a habitat thereof, a fungicidally effective amount of a compound according to claim 1.

13. The method according to claim 12, wherein such compound is

N-(fluorodichloromethylsulphenyl)-N,N$^1$-bis-(4-chlorophenyl)-urea,

N-(fluorodichloromethylsulphenyl)-N-(4-chlorophenyl)-N$^1$-(3,4-dichlorophenyl)-urea, N-(fluorodichloromethylsulphenyl)-N-(3-chlorophenyl)-N$^1$-4-chlorophenyl)-urea, N-(fluorodichloromethylsulphenyl)-N-(3,4-dichlorophenyl)-N$^1$-(4-methoxyphenyl)-urea, N-(fluorodichloromethylsulphenyl)-N-(3-trifluoromethylphenyl)-N$^1$-(4-methoxyphenyl)-urea, N-(fluorodichloromethylsulphenyl)-N-(3,4-dichlorophenyl)-N$^1$-(3-methoxyphenyl)-urea or N-(fluorodichloromethylsulphenyl-N-(4-chlorophenyl)-N$^1$-(4-methoxyphenyl)-urea.

* * * * *